United States Patent [19]

Moore et al.

[11] Patent Number: 5,712,559
[45] Date of Patent: Jan. 27, 1998

[54] CATHODIC PROTECTION REFERENCE CELL AND CORROSION SENSOR

[75] Inventors: Clifford G. Moore, Arcadia; Steven L. Stricklin, Anaheim, both of Calif.

[73] Assignee: Rohrback Cosasco Systems, Inc., Santa Fe Springs, Calif.

[21] Appl. No.: 512,485

[22] Filed: Aug. 8, 1995

[51] Int. Cl.$^6$ .................. G01R 27/20; G01N 27/28; G01N 27/42
[52] U.S. Cl. .................. 324/71.1; 324/425; 324/450; 324/700; 324/72; 204/404; 422/53
[58] Field of Search .................. 324/425, 446, 324/449, 450, 693, 694, 696, 700, 722, 724, 71.1, 71.2, 72; 204/404; 422/53

[56] References Cited

U.S. PATENT DOCUMENTS

| | | | |
|---|---|---|---|
| 3,320,570 | 5/1967 | Lied, Jr. | 324/700 |
| 3,358,229 | 12/1967 | Collins | 324/700 |
| 3,999,121 | 12/1976 | Taylor, Jr. | 324/323 |
| 4,080,565 | 3/1978 | Polak et al. | 324/71.1 |
| 4,133,734 | 1/1979 | Polak et al. | 204/404 |
| 4,338,563 | 7/1982 | Rhoades et al. | 324/700 |
| 4,481,474 | 11/1984 | Gerrit | 324/425 |
| 4,627,905 | 12/1986 | Garner et al. | 204/404 |
| 4,755,744 | 7/1988 | Moore et al. | 324/700 |
| 4,839,580 | 6/1989 | Moore et al. | 324/700 |
| 5,006,786 | 4/1991 | McKubre et al. | 324/71.2 |
| 5,144,247 | 9/1992 | Speck | 324/425 |
| 5,243,297 | 9/1993 | Perkins et al. | 324/700 |
| 5,469,048 | 11/1995 | Donohue | 324/71.1 |
| 5,596,267 | 1/1997 | Lara et al. | 324/71.1 |

OTHER PUBLICATIONS

Rohrback Cosasco Systems, Inc., Bulletin #200-B, "Corrosometer® Probe Selection Guide", Date Unavailable.

*Primary Examiner*—Maura K. Regan
*Assistant Examiner*—Glenn W. Brown
*Attorney, Agent, or Firm*—Renner, Otto, Boisselle, Sklar

[57] ABSTRACT

A combination and unitary corrosion monitor and reference cell for cathodic protection systems includes an elongated tubular metal element of the same material as the structure to be protected and a reference cell on one end of the tubular element, adapted to be buried or submerged in an electrolyte. The tubular element includes resistance connections along its length and a reference resistance element sealed inside. Ratiometric resistance measurements enable the extent of corrosion and corrosion rates to be determined with automatic compensation for temperature changes. Both the resistance measurements and the potential measurements from the cell may be taken from the same test station or location.

30 Claims, 2 Drawing Sheets

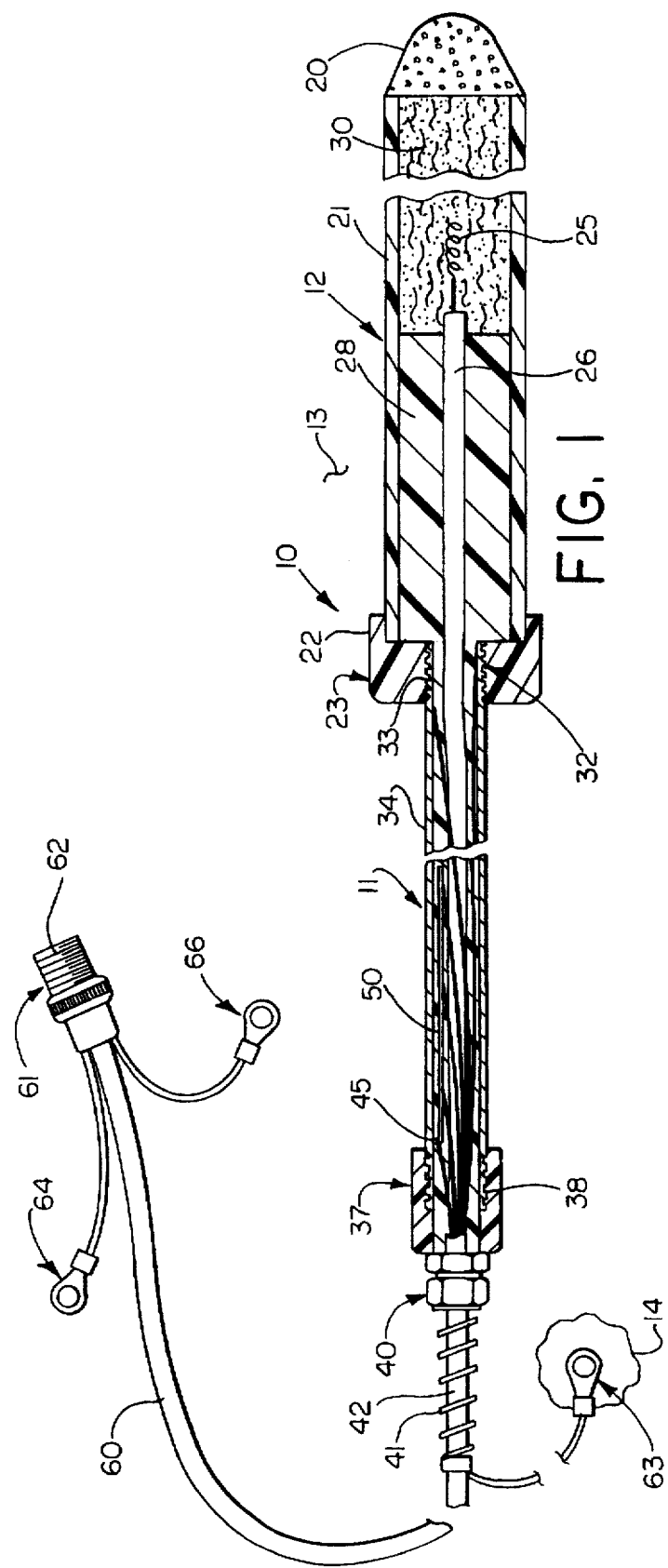
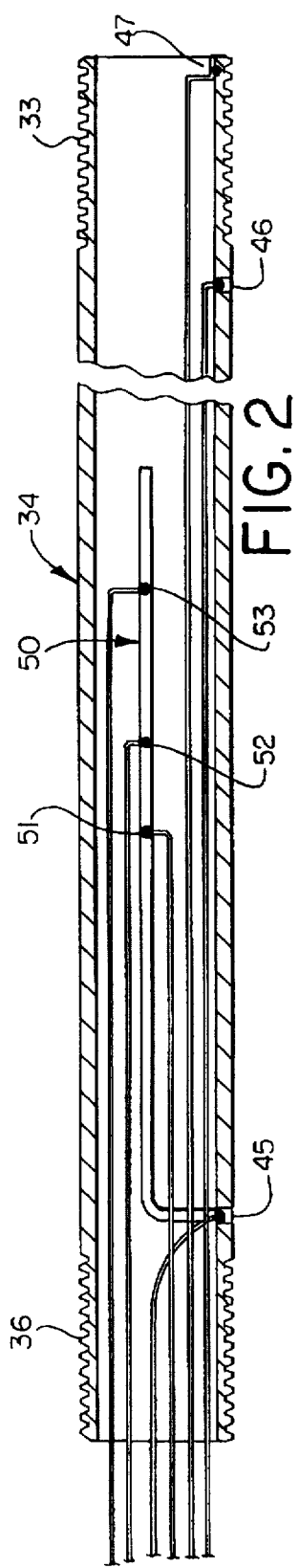

CATHODIC PROTECTION REFERENCE CELL AND CORROSION SENSOR

DISCLOSURE

This invention relates generally as indicated to a combination cathodic protection system reference cell and corrosion sensor, and more particularly to a unitary device for measuring the electrical potential of a protected structure such as a pipeline, and also for monitoring or evaluating its corrosion or corrosion rate.

BACKGROUND OF THE INVENTION

Reference cells are widely used in the cathodic protection industry to evaluate electrical potentials of buried or submerged structures such as pipelines, and thus the effectiveness or level of cathodic protection being provided. Such reference electrodes are usually provided to the point of redundancy when a cathodic protection system is installed, especially where electrolyte conditions (soil) may vary. They are generally associated with one or more test stations and may be difficult and costly to replace or install. In some applications, they should have a useful life as long as or longer than the structure being protected.

There are many types of reference electrodes, and the type of reference electrode may vary depending on the application, such as whether the electrode is to be used in concrete, earth or water. Such electrodes may be, for example, copper/copper sulfate, silver/silver chloride, or zinc/zinc sulfate. It is important, however, that such cells retain their accuracy over many years. Some cells are used as a signal source for automatically controlled systems, and unreliable signals create many problems.

Several types of accurate, long lived cells are sold by Harco Technologies Corporation of Medina, Ohio, under the trademarks PERMACELL® and PERMACELL® PLUS. PERMACELL® is a registered trademark of Harco Technologies Corporation. Such cells may utilize a plastic tube with a porous ion trap at one end, or a ceramic mostly porcelainized capsule which provides a long electrical path. The capsule is surrounded by a thixotropic gel contained in a semipermeable membrane or sack. The capsule is illustrated in Carlson U.S. Pat. No. 5,370,783. The cell may be sold with the test station and the reference cell and test station are packaged and tested as a system before installation.

Some reference electrodes include auxiliary electrodes used to eliminate ohmic components in instant off measurements or evaluations of the polarization potential. An example is seen in Polak et al. U.S. Pat. No. 4,080,565.

Corrosion rates are widely monitored by probes such as the well known CORROSOMETER® probes sold by Rohrback Cosasco Systems, Inc. of Santa Fe Springs, Calif. CORROSOMETER® is a registered trademark of Rohrback Cosasco Systems, Inc. Such probes are widely used internally in pressure vessels and pipelines. They may also be used externally and in the laboratory and in other applications. Such probes generally include an exposed measurement element such as a small cylinder, or a U-shaped strip, tube or wire of the same metal or alloy of the structure being protected, and a sealed reference section. Examples of such probes may be seen in prior U.S. Pat. Nos. 5,243,297, 4,755,744 and 4,338,563.

If the probe is installed inside the vessel or pipeline, complex fittings and tools are required. If the probe is installed externally, excavation placement, conduit, and connections for instrumentation are still required. Its relationship to reference cells must also be considered, particularly if the readings from both are to be used in any comprehensive surveys or computer modelling studies of corrosion rates or the effectiveness of a cathodic protection system.

Another problem with probes is selecting the proper probe sensitivity. A more sensitive probe responds more quickly to system upsets, but the exposed element will corrode away more rapidly requiring replacement more frequently.

In order to do really comprehensive engineering surveys or evaluations of cathodic protection systems, it would be helpful to have a corrosion rate monitor associated with each or at least some reference electrodes, so that both are in the same electrolyte (soil conditions), and that measurements from both can be taken from the same test station or monitoring instrumentation. It would also be helpful if the corrosion rate monitor had high sensitivity and a long useful life which substantially matched that of the reference electrode.

SUMMARY OF THE INVENTION

An assembly in a unitary device includes a combination of an electrical resistance corrosion sensor and an electrochemical reference cell. The assembly is used to evaluate the electrical potential of structures or pipelines relative to the surrounding environment and hence the level of cathodic protection, and also evaluate the total corrosion or corrosion rate of the protected structure. Such evaluations can be made from the same location in the environment and the information can be obtained from the same test station.

The reference cell portion of the invention may be any commonly used reference cell for use in concrete, earth or water, for example. Typical cells are copper/copper sulfate, zinc/zinc sulfate, and silver/silver chloride. The cells may be tubular elements with a porous plug or a ceramic capsule providing a salt bridge connection to the surrounding environment.

The corrosion sensor is a tubular element and an extension of the reference cell, and both are sealed and secured together. The corrosion sensor tube element is made of the same material as the structure being protected. Both ends of the tubular element are threaded and provided with non-conductive plastic caps which seal the tubular element. The entire exterior of the tubular element from cap-to-cap is exposed to the environment or electrolyte and is attached to yet spaced from the reference electrode in the same environment.

The tube is provided with electrical connections at three axially spaced locations which measure the resistance axially of the tubular element. A reference element is sealed in the tubular element and thus not exposed to the environment. Such reference element assembly is a wire extending axially inside the tubular element, and resistance measurement connections are made at three points along the wire. The wire is connected to the tubular element at one of the three spaced locations on the tubular element.

The tubular measurement element will increase in resistance as the cross-sectional area decreases due to corrosion, and measurement of the corrosion metal loss is obtained by a ratiometric comparison of the two measured resistances.

The electrical resistance of metal tubular section may be expressed by the formula:

$$R = \rho \frac{L}{A}$$

where:

ρ is the intrinsic electrical resistivity of the material;

L is the length of the section; and

A is the cross-sectional area of the section

The intrinsic resistivity, ρ, varies from alloy to alloy and is temperature dependent. For a given alloy at constant temperature, the electrical resistance of a fixed-length specimen increases as the cross-sectional area decreases. Consequently, the measurement of electrical resistance may be used to determine metal loss.

Compensation for change of resistivity ρ with temperature is achieved by the use of the reference wire element which is protected from the corrosion process. As the electrical resistance of the tubular element increases with temperature, so does the electrical resistance of the reference wire element. However, the resistance ratio of the two elements remains unchanged, thereby providing automatic compensation for temperature changes.

The tubular element exposed in the electrolyte near the reference cell is connected to the structure to be at the same potential, and accordingly, the total corrosion or corrosion rate of the tubular element will simulate that of the structure. All potential and resistance readings may be taken from a common test station or instrumentation. The complete interior and both ends including the connections to the tubular element are sealed and encapsulated. The connection between the tubular element and reference cell is also sealed and encapsulated. The wiring to the test station and structure is part of the assembly and is packaged and factory tested before shipment. The test station may consist of a protected multipin connector to which the required instrumentation is attached.

To the accomplishment of the foregoing and related ends the invention, then, comprises the features hereinafter fully described and particularly pointed out in the claims, the following description and the annexed drawings setting forth in detail certain illustrative embodiments of the invention, these being indicative, however, of but a few of the various ways in which the principles of the invention may be employed.

BRIEF DESCRIPTION OF THE DRAWINGS

FIG. 1 is an axial section partially broken away of a sensor and cell assembly in accordance with the present invention;

FIG. 2 is an enlarged broken section of the tubular sensor element showing the resistance connections and the reference element.

DESCRIPTION OF THE PREFERRED EMBODIMENT

Figure 3:
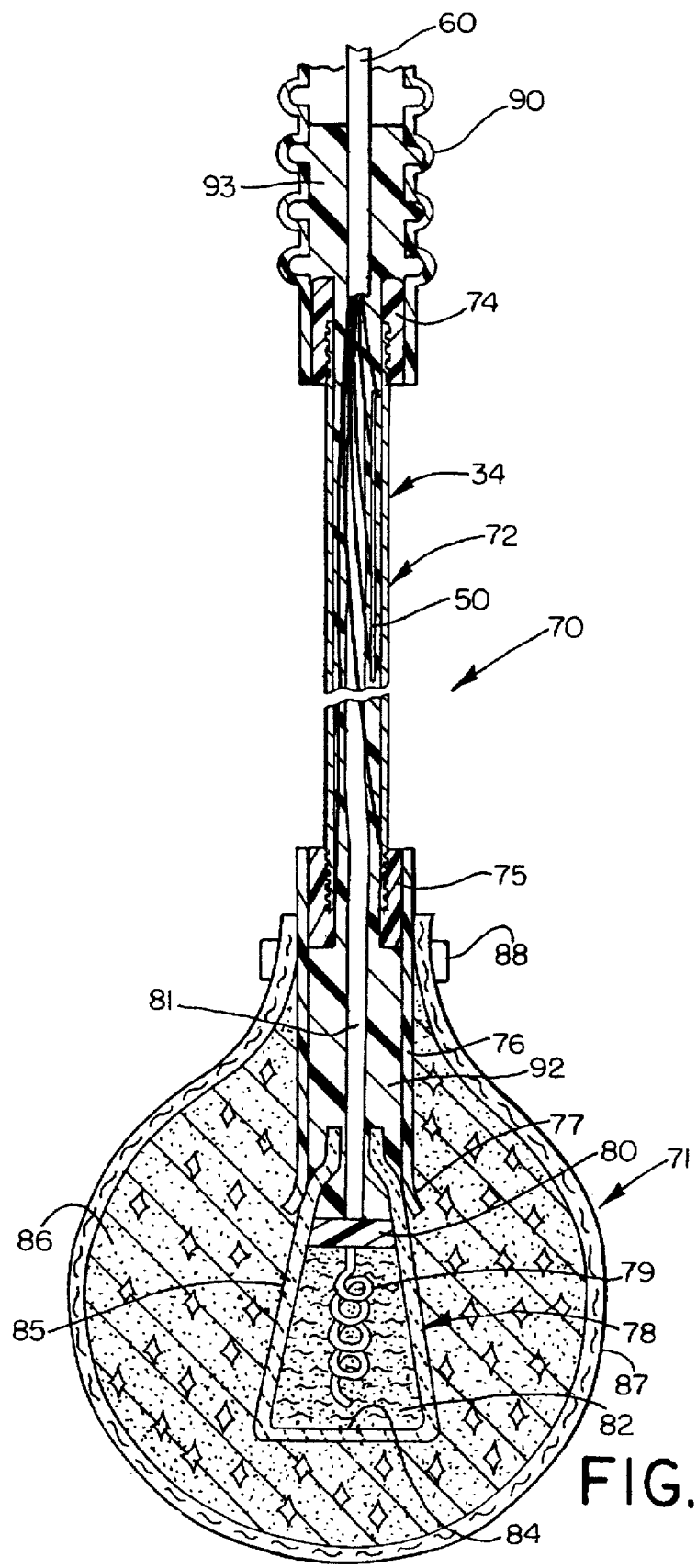
FIG. 3 is a view like FIG. 1 but illustrating a different type of reference cell.

Referring initially to FIG. 1, there is illustrated a combination sensor-cell shown generally at 10. The unitary device includes a corrosion sensor shown generally at 11 and a reference cell shown generally at 12. The reference cell 12 of the unitary structure is an electrochemical reference cell which can be used to evaluate the electrical potential of structures or pipelines relative to the surrounding environments such as the soil, water or concrete in which it is buried or immersed. The electrolyte is shown generally at 13 and surrounds the entire unitary assembly 10. The electrical resistance corrosion sensor 11 is connected to the structure or pipeline under cathodic protection. Such structure is shown schematically at 14 and is buried or immersed in the electrolyte 13. In a conventional impressed current cathodic protection system, a DC current is impressed from anodes, not shown, to the structure 14 to mitigate the electrolytic corrosion which would otherwise occur. As indicated, reference cells are widely used to determine the electrical potential or polarization potential, and to monitor and control the cathodic protection system.

In FIG. 1, there is illustrated one tubular type of reference cell which on its end is provided with a porous generally conical plug 20 which may be ceramic or wood, for example. The plug is sometimes called an ion trap and closes one end of a tubular body 21 of the reference cell. The tubular body of the reference cell is typically a non-conductive plastic such as PVC. The opposite end of the tubular body 21 is telescoped within skirt 22 of plastic sealing cap 23.

The interior of the tubular body 21 contains the metal element of the electrode which is illustrated at 25. The element 25 is a pure metallic electrode and is normally a coiled wire or strip of copper, silver or zinc. The exposed electrode extends axially from an insulated electrical lead seen at 26. The electrode 25 is held centered in the tubular housing 21 by a rigidified potting or sealing compound shown generally at 28. The sealing compound is non-porous and completely fills and seals the interior of the reference cell. The material 28 may be an epoxy or other non-porous inert material which serves a number of purposes. One purpose is to create a tubular dam to contain the electrolyte portion 30 of the cell surrounding the exposed electrode within the housing. The electrolyte component of the reference cell is generally a super saturated solution of copper sulfate, silver chloride or zinc sulfate. The electrical path from the electrode 25 to the surrounding electrolyte 13 is only through the porous nose plug 20.

In addition to serving as a dam for the cell electrolyte 30, the non-porous sealing material 28 also keeps the electrode 25 centered, and prevents inward leakage or contamination from environmental fluids. The material 28 also serves to assist in the joining of the parts 21 and 23, locking and sealing the inner end of the tubular housing 21 to the cap 23.

It is noted that the cap 23 is internally threaded as indicated at 32 and such threads match the external threads 33 on one end of tubular metal element 34 which is a principal component of the sensor 11. The tubular element 34 is preferably of the same metal or material as the pipe or structure 14 being protected. Such material is most commonly mild steel.

The opposite end of the tubular element 34 is provided with external threads seen at 36 in FIG. 2, and on such threaded end, there is provided a plastic end cap 37 having internal threads 38. The end caps function as a cover for the connections between the sensor 11 and the reference electrode as well as the cable to the monitoring or test location. It is noted that both caps 23 and 37 extend axially beyond the tubular element 34 and that the non-porous sealing compound 28 extends from the reference cell completely axially through the tubular element 34, being contained beyond the ends of such tubular element by the axial extensions provided by the caps. Accordingly, the entire interior surface, including the ends of the tubular element, is sealed by the compound 28. Between the end caps 23 and 37, the exterior surface of the tubular element 34 is exposed to the environment or electrolyte 13, as is the structure 14.

Beyond the end cap 37, there is provided a cable sealing gland 40 which further ensures against leakage of environmental fluids. If desired, a stiffening spring shown generally at 41 may surround the exiting cable or harness 42 to reduce sharp flexures of the cable at the sealing gland 40.

Referring now to FIG. 2, it will be seen that the tubular element 34 is provided with three internal electrical connections indicated at 45, 46 and 47. Also connected to the tubular element interior connection 45 is a reference wire element 50 which extends axially within the tubular element 34. The reference element is preferably a wire of the same or quite similar material as the measuring element and electrical connections are made to the reference element along its axial extent at three locations illustrated at 51, 52 and 53. Because the reference element 50 is sealed inside the tubular element 34, it will not be subject to corrosion and electrical resistance measurements along the reference element serve as a reference for electrical measurements made along the tubular element 34, the entire exterior surface of which between the caps 23 and 37 is exposed to the electrolyte or environment of the structure being protected. AC current will be supplied across the leads and resistance measurements taken. The comparisons made will show, over time, not only the rate of corrosion, but also the total corrosion.

The electrical resistance of the metal tubular element 34 may be expressed by the formula:

$$R = \rho \frac{L}{A}$$

where:

$\rho$ is the intrinsic electrical resistivity of the material;
L is the length of the section; and
A is the cross-sectional area of the section The intrinsic resistivity, $\rho$, varies from alloy to alloy and is temperature dependent. For a given alloy at constant temperature, the electrical resistance of a fixed-length specimen increases as the cross-sectional area decreases.

Compensation for change of resistivity $\rho$ with temperature is achieved by the use of the reference wire element which is protected from the corrosion process. As the electrical resistance of the tubular element 34 increases with temperature, so does the electrical resistance of the reference wire element which is closely spaced yet sealed with respect to the tubular element. However, the resistance ratio of the two elements remains unchanged, thereby providing automatic compensation for temperature changes.

The wiring connections or harness for the various resistance measuring points and for the electrode to the reference cell extends through cable 60 to a test station or location 61 at which a multipin connector 62 is provided for interconnection to the standard electrical resistance monitoring instrumentation of the type seen in U.S. Pat. No. 4,338,563.

In order to connect the tubular element 34 to the structure 14, there are provided two alternately employable connections, one of which is shown at 63, while the other is shown at 64. In some applications, it may be more convenient to connect the tubular element 34 to the structure from the monitoring location 61. Also, at the monitoring location, it may be desirable to provide a separate cable connection indicated at 66 for the reference cell. In this manner, the reference cell potential may be measured using the connection 66, while the corrosion or corrosion rate is obtained using the multipin connector 61 with the appropriate monitoring instrumentation, all of which will be mounted at the test station at a convenient and secure location.

In the illustrated embodiment of FIG. 1, it is noted that the tubular element 34 may be approximately 18 inches (45.72 cm) in length and approximately ½ inches (1.27 cm) in diameter. The tubular housing of the reference cell may be approximately twice that length and the vast majority of the housing contains the electrolyte component 30, so that in reality, the pure metallic electrode 25 is spaced substantially from the porous nose plug 20.

Referring now the embodiment of FIG. 3, there is illustrated a combination reference cell and corrosion monitoring sensor shown generally at 70. The instrument comprises the electrochemical reference cell shown generally at 71, and the corrosion monitor or sensor shown at 72. The corrosion sensor 72 is in every respect the same as that shown in FIG. 1 and includes the tubular element 34, and the interiorly sealed reference element 50. The tubular element includes axially projecting plastic end caps 74 and 75 on each end, threaded thereto.

Extending from and sealed to the plastic cap 75 is a plastic tube 76 which has one end slightly flared as indicated at 77, surrounding and sealing such tube to ceramic capsule 78. Inside the capsule is a pure metallic electrode 79 which extends through plug 80 and through insulated lead 81 axially through the corrosion sensor 72. Within the ceramic capsule is preferably super saturated solution of copper sulfate seen at 82. Silver chloride or zinc chloride may also be used. Both the interior and the exterior of the ceramic capsule 78 are porcelainized or glazed with the exception of small windows shown on the interior at 84 and the exterior at 85. The entire cell is surrounded by a stabilized hygroscopic thixotropic gel 86, contained in a microperforated filter bag 87, and cinched and secured at 88 to the plastic tube 76.

The opposite or upper cap 74 is sealed to one end of a corrugated tube 90 which surrounds and protects the cable 60 to the test station or multipin connection. A non-porous potting or sealing compound such as the noted epoxy, completely fills the tube 76 as seen at 92 and also fills the neck of the capsule 78 above the plug 80. This non-porous sealing material extends throughout the interior of the tubular element 34 and upwardly into the corrugated tube 90 as shown at 93. Accordingly, the sealing compound not only seals the complete interior of the tubular element 34 of the corrosion sensor 72, but also facilitates the connection at each end of the sensor to the reference cell 71 and corrugated tube 90, respectively. An example of such a ceramic reference cell may be seen in Carlson U.S. Pat. No. 5,370,783. Such cells including the reference cell, corrugated tube and an integrated test station are sold by Harco Technologies Corporation of Medina, Ohio, under the trademark PERMACELL® PLUS.

It can now be seen that there is provided a unitary sensor and reference cell combination which can be located together and read or monitored from the same test station or location. The assembly provides the capability of measuring the pipe or structure potential with the reference cell and the capability also to measure corrosion loss as well as determine corrosion rate from the corrosion sensor. The later measurements would correlate to long term corrosion losses of the pipe or structure to which it is connected.

The information provided is particularly useful in a wide variety of determinations which can be made concerning the corrosion or potential corrosion of buried or submerged structures, and the effectiveness of cathodic protection on such structures.

Although the invention has been shown and described with respect to certain preferred embodiments, it is obvious that equivalent alterations and modifications will occur to others skilled in the art upon the reading and understanding of this specification. The present invention includes all such equivalent alterations and modifications, and is limited only by the scope of the claims.

What is claimed is:

1. In combination a reference cell for measuring the electrical potential of a structure cathodically protected in an electrolyte, and a unitary corrosion sensor, said sensor comprising a metal tubular element of the same metal as the structure and exposed to the electrolyte at the same general location with respect to the structure as the cell, and means to measure the resistance through the tubular element and through a reference element sealed inside the tubular element to monitor corrosion and corrosion rate, and said cell and sensor each having common connections to a test station.

2. A combination as set forth in claim 1 wherein said metal tubular element is electrically connected to the structure being protected.

3. A combination as set forth in claim 1 wherein both ends of said metal tubular element are externally threaded, and plastic caps mounted on both ends of said metal tubular element, said cell being secured to one of said caps.

4. A combination as set forth in claim 3 wherein both caps project beyond the ends of said tubular element.

5. A combination as set forth in claim 4 wherein the interior of the entire tubular element from the outer ends of said end caps is encapsulated and sealed in a potting compound.

6. A combination as set forth in claim 5 wherein said potting compound extends at least partially into said cell to assist in joining the cell to the sensor.

7. A combination as set forth in claim 6 wherein said cell includes a plastic tubular element telescoped with respect to one of said end caps.

8. A combination as set forth in claim 7 wherein insulated wiring for said cell extends axially through said metal tubular element.

9. A combination as set forth in claim 4 including a wiring harness extending from the other of said caps to a test station, and connections extending from both ends of the wiring harness to connect said metal tubular element to said structure.

10. A combination as set forth in claim 1 including resistance measuring connections on the inside of said metal tubular element at two axially spaced locations.

11. A combination as set forth in claim 10 including a reference wire extending axially of the interior of the metal tubular element.

12. A combination as set forth in claim 11 wherein said reference wire is connected at one end to one of said resistance measuring connections on the inside of said metal tubular element.

13. A combination as set forth in claim 12 including at least two resistance measuring connections along said reference wire.

14. A combination as set forth in claim 13 including at least three resistance connections along the interior of said metal tubular element, two being adjacent the inner edges of said plastic caps, while the third is adjacent an end of said metal tubular element.

15. A combination as set forth in claim 14 including at least three resistance connections along the axial length of said reference wire.

16. A corrosion sensor and reference cell assembly for cathodic protection systems of tubular construction adapted to be buried or submerged in an electrolyte surrounding the cathodically protected structure, said sensor comprising a metal tubular exposed element with the cell on one end thereof, and wiring for both the cell and sensor extending from the other end thereof to a test station.

17. An assembly as set forth in claim 16 wherein said metal tubular element is electrically connected to the structure being protected.

18. An assembly as set forth in claim 16 wherein both ends of said metal tubular element are externally threaded, and plastic caps mounted on both ends of said metal tubular element, said cell being secured to one of said caps.

19. An assembly as set forth in claim 18 wherein both caps project beyond the ends of said tubular element.

20. An assembly as set forth in claim 19 wherein the interior of the entire tubular element from the outer ends of said end caps is encapsulated and sealed in a potting compound.

21. An assembly as set forth in claim 20 wherein said potting compound extends at least partially into said cell to assist in joining the cell to the sensor.

22. An assembly as set forth in claim 20 wherein said cell includes a plastic tubular element telescoped with respect to one of said end caps.

23. An assembly as set forth in claim 22 wherein insulated wiring for said cell extends axially through said metal tubular element.

24. An assembly as set forth in claim 19 including a wiring harness extending from the other of said caps to a test station, and connections extending from both ends of the wiring harness to connect said metal tubular element to said structure.

25. An assembly as set forth in claim 16 including resistance measuring connections on the inside of said metal tubular element at two axially spaced locations.

26. An assembly as set forth in claim 25 including an interior reference wire extending axially of the metal tubular element.

27. An assembly as set forth in claim 26 wherein said reference wire is connected at one end to one of said resistance measuring connections on the inside of said metal tubular element.

28. An assembly as set forth in claim 27 including at least two resistance measuring connections along said reference wire.

29. An assembly as set forth in claim 28 including at least three resistance connections along the interior of said metal tubular element, two being adjacent the inner edges of said plastic caps, while the third is adjacent an end of said metal tubular element.

30. An assembly as set forth in claim 29 including at least three resistance connections along the axial length of said reference wire.

* * * * *